United States Patent
Pearson, Jr. et al.

(10) Patent No.: US 6,181,766 B1
(45) Date of Patent: Jan. 30, 2001

(54) DIGITAL ENCODING OF RF COMPUTERIZED TOMOGRAPHY DATA

(75) Inventors: Phil E. Pearson, Jr., Waukesha; James K. Omick, New Berlin, both of WI (US)

(73) Assignee: General Electric Company, Milwaukee, WI (US)

(*) Notice: Under 35 U.S.C. 154(b), the term of this patent shall be extended for 0 days.

(21) Appl. No.: 09/139,697

(22) Filed: Aug. 25, 1998

(51) Int. Cl.$^7$ .................................................. A61B 6/03
(52) U.S. Cl. ........................ 378/15; 378/98.8; 378/901; 382/131
(58) Field of Search .................... 378/15, 19, 4, 378/98.8, 901; 382/131, 132; 37/278, 339

(56) References Cited

U.S. PATENT DOCUMENTS

| | | |
|---|---|---|
| 5,530,422 | 6/1996 | Harrison . |
| 5,530,423 | 6/1996 | Harrison . |
| 5,530,424 | 6/1996 | Harrison et al. . |
| 5,530,425 | 6/1996 | Harrison . |
| 5,577,028 | * 11/1996 | Gordon et al. ........................ 370/278 |
| 5,579,357 | 11/1996 | Harrison . |
| 5,600,697 | 2/1997 | Harrison . |
| 5,646,962 | 7/1997 | Harrison . |
| 5,737,356 | 4/1998 | Harrison et al. . |
| 5,970,113 | * 11/1996 | Crawford et al. ..................... 378/19 |

FOREIGN PATENT DOCUMENTS

| | | |
|---|---|---|
| WO 96/29008 | 9/1996 | (WO) . |
| WO 96/29708 | 9/1996 | (WO) . |

OTHER PUBLICATIONS

New Release, "AMD adds muscle to the corporate backbone with gigbit ethernet," Sep. 22, 1997.

* cited by examiner

Primary Examiner—David P. Porta
Assistant Examiner—Drew A. Dunn
(74) Attorney, Agent, or Firm—Armstrong Teasdale; Christian G. Cabou; Phyllis Y. Price

(57) ABSTRACT

A serial digital bit signal having signal bits occurring in a bit interval and at a signal bit speed, and each signal bit representing, alternatively, a first logic state and a second logic state, is transferred across a rotating interface by encoding each first logic state bit with a digital radio frequency (RF) carrier signal and coupling the encoded signal across the interface with an RF slipring.

28 Claims, 5 Drawing Sheets

DIGITAL ENCODING OF RF COMPUTERIZED TOMOGRAPHY DATA

BACKGROUND OF THE INVENTION

This invention relates to computerized tomography (CT) systems, and more particularly to communication of high data rate signal images across the CT rotating interface.

As known, CT systems are used to obtain non-invasive sectional images of test objects. The most common use is to provide internal images of human patients for medical analysis and treatment. In operation, the object or patient is positioned on a table within a central aperture of a rotating frame, or gantry, which is supported within a stationary frame. The gantry includes an x-ray source and a detector array positioned on opposite sides of the aperture, within the system's imaging plane, and each rotate with the gantry around the object being imaged. At each of several angular positions along the rotational path the x-ray source emits a collimated beam which passes through the object and is received by the detector array. Sensors within the detector array produce electrical signal indications of the x-ray intensity incident at their surface, and these signals are collated by circuitry within the rotating frame into a set of image data at each angle. Each image data set is referred to as a view, and the plurality of views taken in each revolution, referred to as a scan, are processed by a stationary side computer into a cross sectional image of the object.

It is known to transfer detector data across the rotating gantry interface to the stationary side computer using a non-contact, electromagnetic coupling referred to as an RF (radio frequency) slipring. The data transfer occurs during scanning. There are nominally 1000 views in a full (360°) scan, and a typical maximum gantry slew rate of 360° per second. For a CT system with 752 detector channels, each channel providing a data signal with 16 bit image resolution, the data signal bit speed=(752×1000×16)/1.0=12.03 Mbps. The bit cell time is 83 nano seconds. This is a comparatively slow bit rate, with a corresponding long interval bit cell time, which minimizes the affects of ambient noise on the signal integrity. In these systems the data is amplitude modulated with an RF carrier signal and transmitted through the RF slipring to the stationary side.

In newer CT systems, for reasons related to patient comfort and efficiency, there is an emphasis on reducing the time spent in performing CT scans. This has led to CT designs capable of producing multiple slice images within a single rotation. One such proposed CT system produces four slices per revolution and a gantry slew rate of 720° per second, or 0.5 seconds per revolution. With the same 16 bit element signal resolution and 1000 images per slice per revolution, the resulting data rate is: (752×4×1000×16)/0.5= 96.26 Mbps. With the addition of overhead bits the signal bit rate approaches 110 Mbps with a bit cell time of 9.2 nano seconds. This is nearly an order of magnitude increase in required throughput across the rotating interface.

While RF amplitude modulation is cost effective compared with alternative modulation methods, it is noise susceptible. As the data signal bit speed increases, ambient noise has an increasingly greater effect due to the smaller bit cell times. This reduced cell time causes the data bits to be increasingly susceptible to induced noise, including the loss of or displacement of the data bits, so as to lose synchronization and cause "jitter" in the data stream. It is currently known to use forward error correction (FEC) of the data stream to reduce this noise and jitter, however, FEC is expensive and complex to implement.

BRIEF SUMMARY OF THE INVENTION

An object of the present invention is to provide apparatus and method for coupling high bit speed digital signal data across a rotating interface with lower cost and comparable accuracy to that provided with prior art methods. Another object of the present invention is to provide improved CT apparatus capable of higher image scan rates than that available in the prior art.

According to a first aspect of the present invention, a rotating side serial data signal comprising sequential digital signal bits propagating at a selected bit speed, each bit occurring in an associated data bit interval and each representing, alternatively, a first logic state and a second logic state, is electromagnetically coupled to a stationary side of the rotating interface by modulating each first logic state bit with a digital radio frequency (RF) carrier signal, the coupled data signal being demodulated on the stationary side to restore each such modulated bit to its first side first logic state. In further accord with this aspect of the invention the first side RF modulated signal is electromagnetically coupled to the second side through an RF slipring. In still further accord with this aspect of the invention the digital RF carrier signal digitally encodes each rotating side first logic state of the data signal in an RF digital signal pattern, and the stationary side received data signal is decoded in accordance with a rules based algorithm capable of distinguishing the appearance of a first logic state from the appearance of noise in the received pattern.

In yet still further accord with this aspect of the present invention the RF digital signal pattern comprises N serial pulses at a frequency which is substantially equal to N times the selected bit speed of the data signal. In yet still further accord with this aspect of the invention the N serial pulses are provided on the rotating frame at a selected minimum duty cycle, and the rules based algorithm on the stationary frame decodes the appearance of more than half of the N pulses in a data bit cell time as a first logic state and the appearance of all other numbers of pulses as a second logic state. In yet still further accord with this aspect of the invention the first logic state bits are encoded with a four pulse, fifty percent duty cycle pattern on the rotating frame side, and the stationary frame side algorithm decodes each appearance of three of four and four of four received pulses in a data bit interval as a first logic state, and decodes each appearance of two or less received pulses in a data bit interval as a second logic state.

According to a second aspect of the present invention the RF digital signal pattern is synchronized with the serial data signal on the first side of the rotating interface, thereby minimizing mis-registration of the decoded second side data bits from their associated data bit interval. In further accord with this second aspect of the invention, synchronization is achieved by phase locking the RF digital signal pattern to the serial data signal on both sides of the rotating interface.

According to a third aspect of the present invention, transmitter circuitry on the first side of the rotating surface digitally encodes the serial data signal with an RF digital signal pattern and provides the encoded signal as plural differential signals, each substantially identical and each presented to an associated one of plural transmission lines disposed in cascade over a 360° arc on the rotating side, each such transmission line being arrayed to provide electromagnetic coupling of the RF digital encoded signal therein to a coupler element on the second side of the interface, the coupler presenting the coupled signal to receiver circuitry which decodes and restores the serial data signal to its original state. In further accord with this aspect of the invention, the transmitter circuitry and receiver circuitry each comprise emitter coupled logic (ECL) circuit elements. In still further accord with this third aspect of the invention the ECL elements of the transmitter and receiver circuitry comprise positive ECL (PECL) circuit elements.

The present invention provides for high integrity transmission of high bit speed data signals across a rotating interface. The transmission occurs through digital encoding of the serial bit data signal with an RF digital signal pattern, which crosses the interface on an RF slipring. The benefits of this digital encoding include the replacement of expensive analog RF elements for the slipring's transmitter and receiver circuitry with lower cost digital circuit elements, and the use of encoding to substantially reduce the occurrence of data errors due to noise. Furthermore, synchronizing the RF digital encoding pattern with the serial bit data minimizes data stream jitter due to overlap or underlap of the decoded signal bits within their respective bit cells.

Although the invention is highly suitable for use with high scan rate CT equipment, it may also be used in various other high data rate applications requiring high integrity, high signal speed transmission across a rotating interface. These and various other objects, features, and advantages of the present invention will become more apparent in light of the following detailed description of a best mode embodiment thereof, as illustrated in the accompanying Drawing.

DETAILED DESCRIPTION OF THE INVENTION

Figure 1:
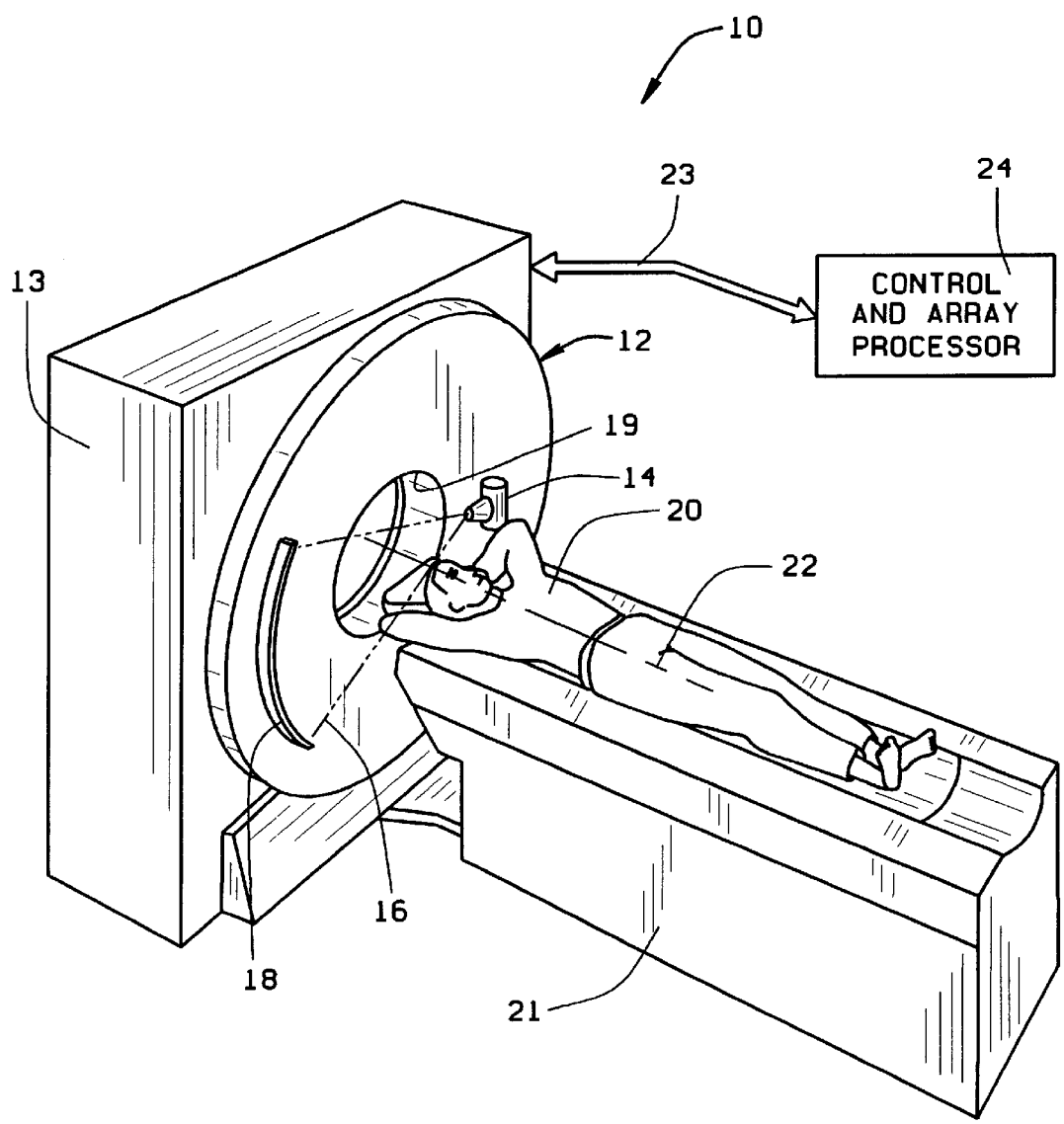
FIG. 1 is an illustrative, perspective view of a CT imaging system in which the present invention may be used.

Referring to FIG. 1, a computerized tomography (CT) imaging system 10 includes a rotating frame, or gantry structure 12, and a stationary support structure 13. The gantry includes an x-ray source 14 for projecting an x-ray beam 16 toward a detector array 18 positioned on the opposite side of a gantry aperture 19. The aperture permits the test object, such as a medical patient 20, to be placed on a platform 21 which may be positioned along the gantry's rotational axis 22. This allows different portions of interest of the test object to be placed within the plane of the gantry, which is the system's image plane.

The gantry is rotated, and at each of a plurality of angular positions along the rotational path, the x-ray source 14 emits the x-ray beam 16, which passes through the test object and is incident at the receiving surfaces of a plurality of detector elements (not individually shown ) of the detector array 18. In response, the detector elements each produce an electrical signal at a magnitude proportional to the intensity of the received rays and, therefore, to the degree of attenuation of the beam after passing through the test object. As described in further detail hereinafter, the signals from each of the elements are presented through lines 23 to a control and array processor 24 which processes the data set values into a composite image of the object at the selected radial position, which is referred to as a view. The aggregate of the views taken over a full revolution of the gantry, otherwise referred to as a scan, are further processed, using known image processing algorithms, into a cross sectional image of the portion of the test object within the image plane.

Figure 2:
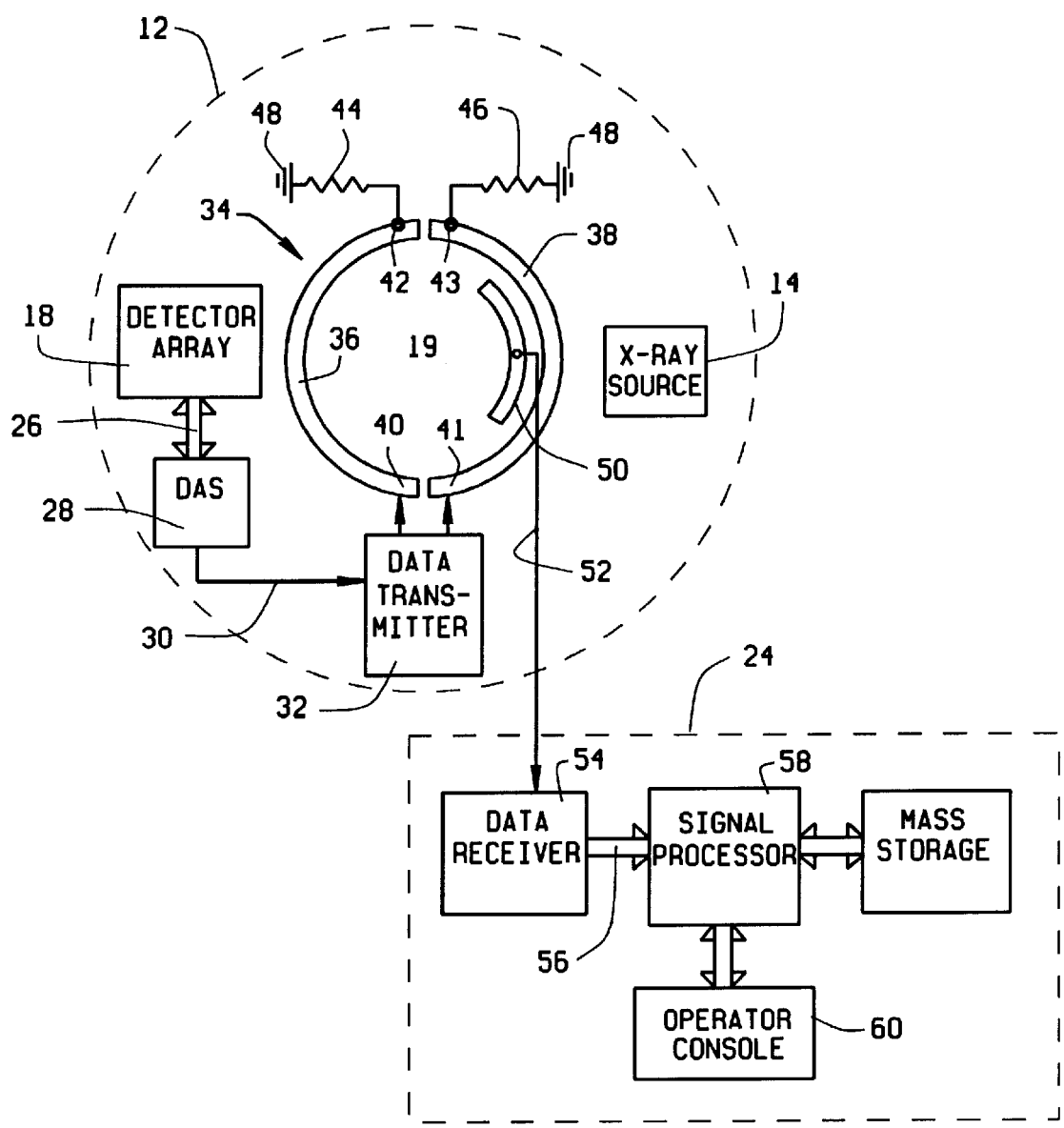
FIG. 2 is a figurative schematic block diagram of portions of the system illustrated in FIG. 1.

Referring now to FIG. 2, which is a simplified, figurative schematic block diagram of a portion of the elements of the system 10 of FIG. 1. For purposes of clarity, only those functional elements necessary for a teaching of the present invention are shown. The signals from the detector array 18 are provided through lines 26 to a data acquisition system (DAS) 28, which converts each signal from an analog signal format into a digital binary signal; typically, with 16 bit resolution. The DAS multiplexes the converted detector channel signals, together with a data clock signal and error checking signal function, into a serial digital bit signal. In the present invention the serial digital bit signal is provided on lines 30 to a data signal transmitter 32 disposed on the rotating frame 12. As described in detailed hereinafter with respect to FIG. 3, the data transmitter digitally encodes the serial data with an RF (radio frequency) pulse pattern, and the RF encoded signal is presented to an electromagnetic coupler, such as an RF slip ring 34 of the type disclosed in U.S. Pat. No. 5,530,424 to Harrison et al, which is assigned to the assignee of this application and which is incorporated by reference herein.

The '424 RF slip ring configuration includes one or more transmission lines disposed on the rotating side of the interface; one coupler segment mounted on the relatively stationary side. Depending on the distance between the stationary coupler and the rotating transmission line, a number of transmission line segments may be required to ensure that the coupler is always in spatial proximity to at least one of the segments to receive the electromagnetic signal. In that case each segment has a length which is a fractional portion of the arc length of the gantry's rotational path. The segments are cascaded, end-to-end around the gantry's rotational axis 22 (FIG. 1); typically along the circumference of the aperture 19 (FIG. 1); such that the aggregate length provides a substantially 360° arc, i.e. a full rotation of the gantry.

In the present embodiment two transmission line segments 36, 38 are used and are mounted in a manner to provide adjacent positioning of first ends 40, 41 and second ends 42, 43 of the transmission lines 36, 38, respectively. Contiguous placement of the ends of each of the transmission lines provides substantial continuity of the electromagnetic coupling along the full rotational path of the gantry.

The data transmitter 32 provides the encoded serial data to the first ends 40, 41 of each of the transmission lines 36, 38. The second ends 42, 43 of each transmission line are connected through terminal impedance's 44, 46 to signal ground 48. A coupler element 50 positioned on the stationery frame (not shown in FIG. 2) in a manner to insure physical proximity of the coupler to one and both of the transmission lines 36, 38 during gantry rotation. The encoded data is electromagnetically coupled through to the coupler 50, as described in the hereinbefore incorporated '424 patent to Harrison et al.

On the stationery frame side, the coupled data signal is provided on lines 52 to the control and array processor 24 (FIG. 1). In the present invention the encoded data is received at a data signal receiver 54. As described in detailed hereinafter with respect to FIG. 4, the signal receiver 54 decodes the serial data using a rules based algorithm and provides the decoded data through lines 56 to a signal processor 58. The signal processor 58 includes signal memory (not shown) for storing the program algorithms which govern the CT processing of the received data in response to operator commands entered through an operator console 60. The algorithms and the resulting processes are well known in the art. In this manner the signal processor collates the decoded image data sets into a composite view associated with the particular angular position of the gantry. The individual views are stored in mass storage device 62 and are retrieved as necessary during processing of the individual views to provide a composite image corresponding to a cross section of the test object.

Figure 3:
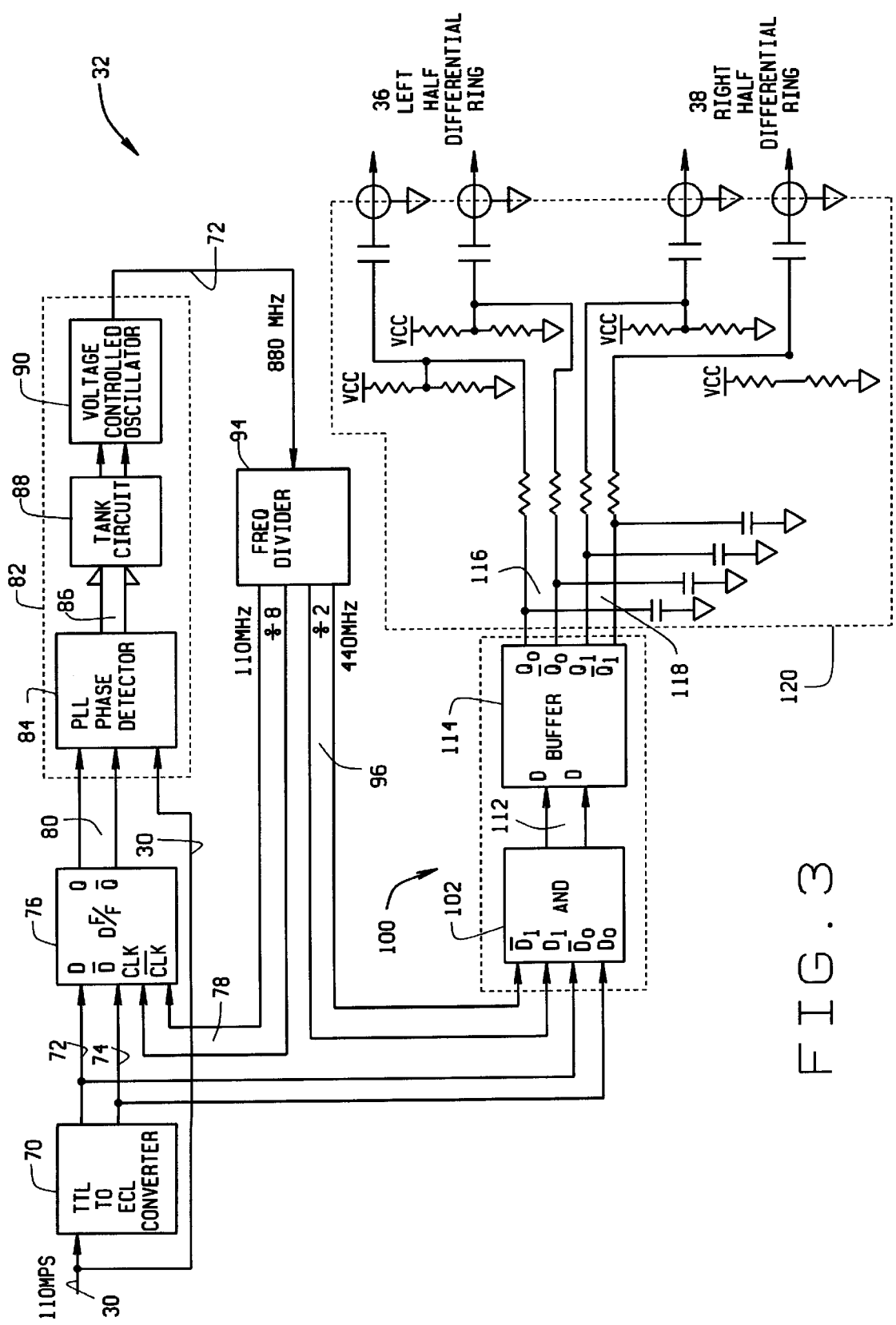
FIG. 3 is a schematic block diagram of one of the elements of the system of FIG. 2.

Referring now to FIG. 3, in the present embodiment the serial data signal on lines 30 from the DAS 28 (FIG. 2) is received at an approximate bit signal speed of 110 Mbps. The DAS data is in $T^2L$ (transistor-transistor-logic) format. In the present invention, at the bit signal speeds involved, the substitution of RF amplitude modulation of the data with RF digital encoding requires high speed digital circuitry. Therefore, according to a second aspect of the present invention, the signal transmitter 32 and signal receiver 54 each comprises digital gate logic functions which are implemented with emitter coupled logic (ECL) devices. In a best mode embodiment the ECL devices used are single gate devices, with gate switching speeds of 250 pico seconds and flip-flop toggling at over 2 Ghz. These devices, which are available from various vendors, including MOTOROLA, Inc. as their ECLinPS Lite (a trademark of MOTOROLA, Inc.), provide high switching speed, single gate devices in small (standard 8 lead SOIC) packages with half the propagation delay of the multi-gate, 28 pin configurations. These characteristics, together with the lower signal switching amplitudes (typical 800 mV output swing into a specified 50 ohm load) provide the necessary bandwidth for the present RF encoding process.

In FIG. 3, the $T^2L$ format data signal from the DAS 28 is presented to a $T^2L$-to-ECL converter 70 and the output ECL formatted data signal (Q and the convolute Q-NOT is provided on lines 72, 74 respectively to D and D-NOT inputs, respectively, of a D edge flip-flop ("flop") 76, such as the MOTOROLA ECL Differential Data and Clock flip-flop, model MC10EL52. The flop 76 is clocked with a 110 MHz taxi clock signal provided on lines 78 (CLK and CLK-NOT). The flop data output is presented on lines 80 to a phase locked loop (PLL) 82 which includes a Phase-Frequency Detector 84 (detector), such as the MOTOROLA model MC12040, and a voltage controlled oscillator (VCO) 90, such as the MOTOROLA model MC12148. The detector 84 also receives the DAS data signal on line 30 and determines the presence of a signal phase difference between the two. A phase difference is quantified as a duty cycle pulse provided on output lines 86 through a tank (resistor capacitor) circuit 88 to a voltage controlled oscillator (VCO) 90.

As known, the VCO 90 provides an output clock signal at a nominal, center frequency which is adjusted upwardly or downwardly based on the magnitude of the phase error signal provided from the detector 84. In the present embodiment the DAS data signal speed is 110 Mbps and, as described hereinafter, the RF encoding frequency is chosen to be 4× the data signal speed, or 440 MHz. Therefore, in the present embodiment, the VCO center frequency is selected at 880 MHz, or approximately eight times the DAS serial data bit speed. The 880 MHz clock signal is provided on line 92 to a frequency divider 94, such as the MOTOROLA MC10EL34 Clock Generation Chip which provides a divide by eight 110 MHz transparent asynchronous xceiver (transceiver) interface taxi clock signal on line 78, and a divide by two 440 MHz RF encoding signal on lines 96. The PLL 82 insures that each of these signals are phase synchronized to the DAS data signal to synchronize the data signal bit edges to prevent overlap or underlap of adjacent bits which can produce image jitter.

In the present invention the serial bit data signal is encoded in a digital pattern at RF carrier signal frequency, which is decoded on the receiver side to restore the signal to its original logic state. This RF encoding carrier signal allows for electromagnetic coupling through the RF slip ring and the digital encoding provides high noise discrimination as well as a simpler, lower cost RF modulating scheme. In a best mode embodiment only one of the two logic states of the serial data signal are encoded. If a first logic state is chosen as the encoded state then, on the receiver side, the absence of encoding implies the presence of the second logic state. Also, to simplify the encoding process in a best mode embodiment, a serial pulsed signal is chosen, which provides a known number of pulses, at a given pulse width and RF pulse repetition frequency (PRF), within the bit time interval of the encoded signal bit.

Figure 4:
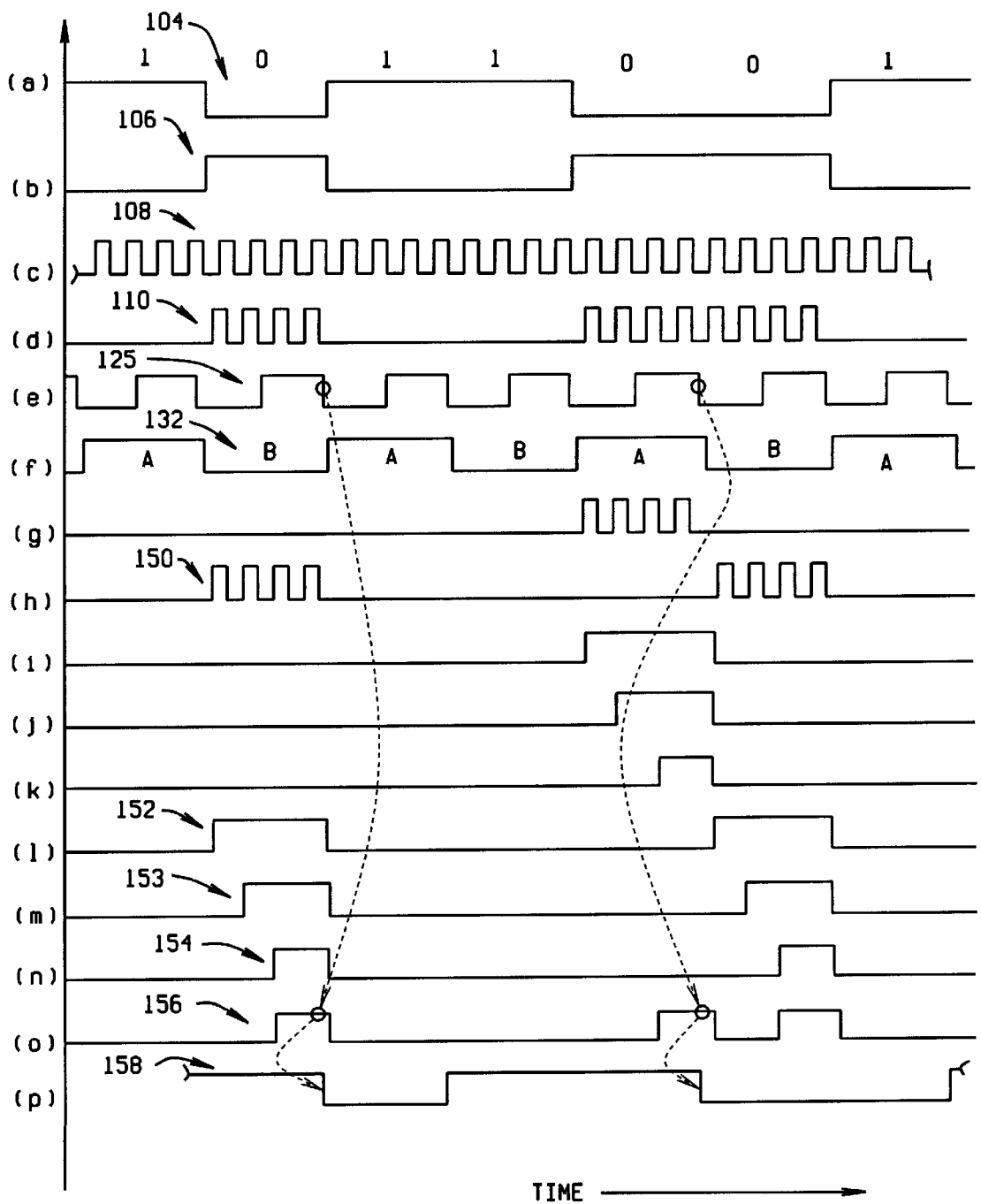
FIG. 4 is a signal waveform illustration used, in conjunction with FIGS. 3 and 5, in the description of operation of the present invention.

Encoding circuit 100, which, in the present embodiment is an AND function, such as the MOTOROLA model MC10EL05 "2 input Differential AND/NAND" gate, which receives the ECL serial bit data signal on lines 72, 74 at the $D_0$-NOT and $D_0$ inputs of the gate. In the present embodiment the logic zero state of the data signal is the bit state chosen for encoding, and the DATA-NOT (the inverse of the data signal) is presented to the Do input of the gate. The AND gate also receives the modulating signal on lines 96 from the frequency divider 94 at the $D_1$-NOT and $D_1$ inputs of the gate. Referring to FIG. 4, illustration (a) illustrates a 1011001 excerpt of the DATA signal waveform 104, illustration (b) is the corresponding DATA-NOT segment waveform 106, and illustration (c) is the 440 MHz modulating signal waveform 108. The gate 102 ANDs the modulating signal with the DATA-NOT signal to provide the corresponding encoded pattern waveform 110 in FIG. 4, illustration (d).

It should be emphasized, that in addition to the serial pulse pattern providing a simple scheme to implement, it also provides a simple pattern from which to detect noise interference. The encoded signal is presented on output lines 112 from the AND gate to a buffer 114, such as a MOTOROLA Differential Fanout Buffer, model MC10EL11. With the two transmission line segments of the RF slipring of the present embodiment, the buffer 114 provides a pair of differential, identical, encoded serial data signal on lines 116 and 118 through a resistor-capacitor impedance matching/filter circuit 120 to the inputs 40, 41 of the left half transmission line segment 36 and right half transmission line segment 38 (FIG. 2).

Figure 5:
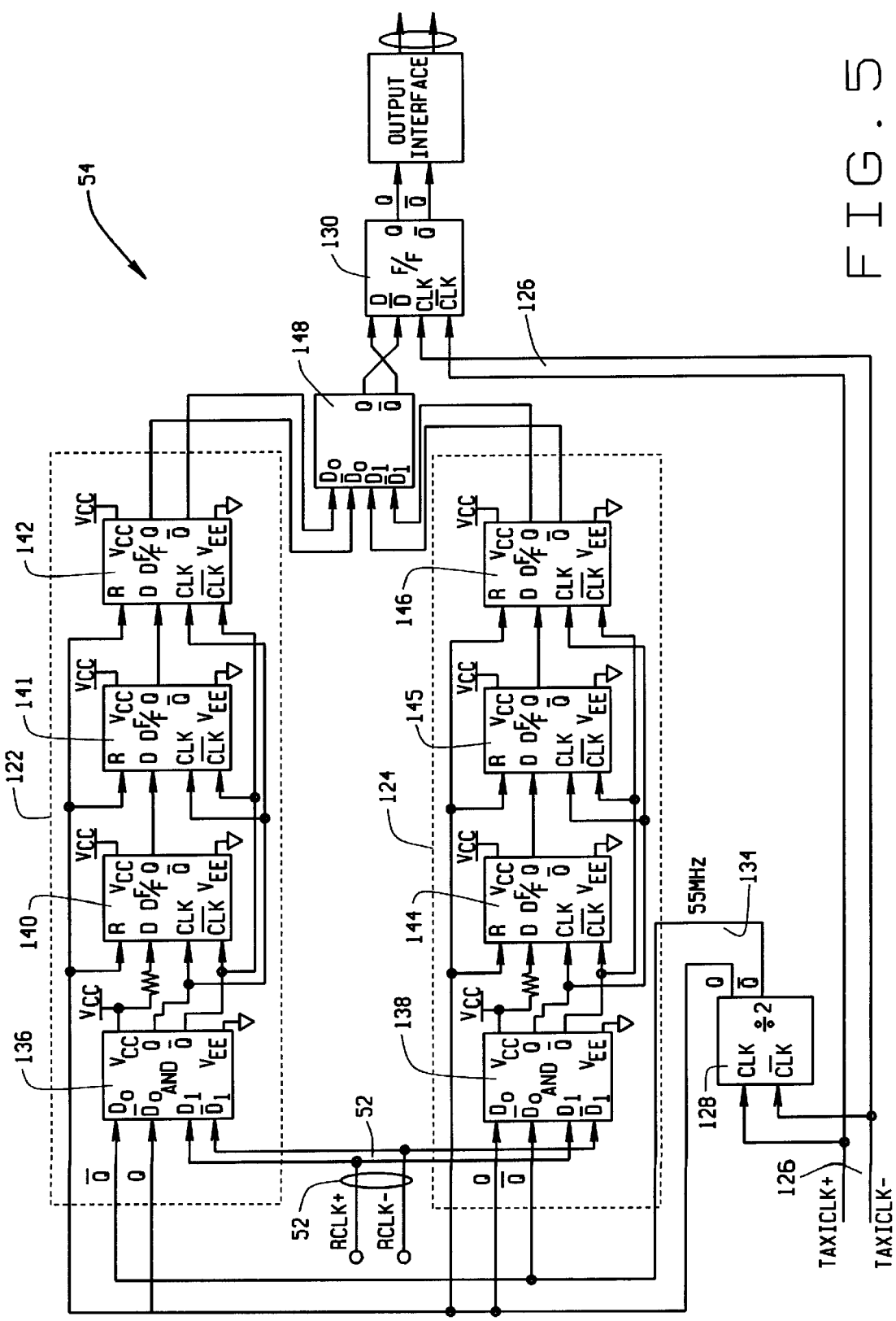
FIG. 5 is a schematic illustration of another element of the system of FIG. 2.

The differential RF encoded data signal is coupled through the RF slip ring as described in the incorporated U.S. Pat. No. 5,530,424 to Harrison et al, received by the slip ring coupler 50, and presented on lines 52 to the data receiver 54 (FIG. 2). Referring now to FIG. 5, in a best mode embodiment the receiver 54 receives the encoded data signal at the input of each of a pair of decoding circuits 122, 124. For descriptive purposes the pair of decoding circuits 122, 124 are referred to as Channel A and Channel B, respectively. Clock recovery circuitry (not shown) recovers the transparent asynchronous xceiver (transceiver) interface clock signal which is shown by the waveform 125 in FIG.

4, illustration (e), and which is presented on lines 126 to a divide by 2 circuit 128 and, inverted, to the CLK-NOT input of a final reclock flip-flop 130.

The use of A and B channels facilitates the 9.2 nano second bit interval of the 110 Mbps data signal by alternating the decoding task on succeeding bit intervals. Therefore, each channel decodes only one of two succeeding giving each channel a cycle time of 18.4 nano seconds. The channels are enabled and disabled by a SELECT channel signal provided by the divider circuit 128 at one-half (i.e. 55 MHz) the (110 MHz) transparent asynchronous xceiver (transceiver) interface clock frequency. The SELECT signal, which is shown by the waveform 132 in FIG. 4, illustration (f), is synchronized to the data signal through synchronization of the taxi clock by the PLL 82 (FIG. 3) in the signal transmitter 32, and is presented (Q and Q-NOT) on lines 134 to the $D_0$ and $D_0$-NOT inputs of AND gates 136, 138 of the A and B channels, respectively.

The A and B channels each include the first element AND gates 136, and 138, followed by cascaded D edge triggered flip-flops 140–142 and 144–146, respectively. The differential Q output of the last flip-flops 142 and 146 are presented to the $D_0$ and $D_1$ inputs of AND gate 148. These AND gates and D flip-flops are the same type ECL gates described hereinbefore with respect to the signal transmitter diagram of FIG. 3. The AND gates 136, 138 are held LOW (logic zero state), which is disabled, whenever the $D_0$ input is HIGH. Therefore, the SELECT Q signal is presented to the $D_0$ input of AND 138 and the SELECT Q-NOT is presented to the $D_0$ of AND 136. This allows the alternate toggling of the channels, which is functionally shown in the SELECT signal waveform 132 (FIG. 4, illustration (f)) with alternate states of the waveform labeled A and B. Referring to FIG. 4, illustration (d), the occurrence of the first series of four pulses, corresponding to the logic zero state of the data signal waveform 104 in illustration (a), is decoded by the channel B decoding logic 124 with the LOW state of the SELECT Q waveform 132 (illustration (f)).

With a LOW Do input to the AND gate 138, the gate Q output follows the encoded data signal to provide the four pulse output shown in waveform 150 of FIG. 4, illustration (h). The AND gate Q output is presented to the CLK inputs of each of the D flip-flops 144–146, causing each to toggle HIGH in succession on the first three of the data signal's four pulses, as shown by the waveforms 152–154 of illustrations (1) through (n). The third pulse also sets the output of the AND gate 148 HIGH, as shown by the waveform 156 of FIG. 4, illustration (o). The Q and Q-NOT outputs of gate 148 are inversely presented to the D-NOT and D inputs, respectively, of the output D flip-flop 130, which also receives the transparent asynchronous xceiver (transceiver) interface clock signal (waveform 108, FIG. 4, illustration (c)) at its CLK-NOT input.

With the Q output of the gate 148 HIGH, the Q-NOT is LOW, setting the D input to the flop 130 LOW. On the next LOW to HIGH transition of the CLK-NOT input (the HIGH to LOW transition of the transparent asynchronous xceiver (transceiver) interface clock signal waveform 108 of FIG. 4, illustration (c)), the flop 130 transitions LOW. With the LOW to HIGH transition of the SELECT signal (132, FIG. 4, illustration (f)) the AND gate 148 goes LOW and on the next LOW to HIGH transition of the transparent asynchronous xceiver (transceiver) interface clock-NOT, which corresponds to one bit interval of the data signal, the Q output of the flop 130 goes high. The output of the flop 130, i.e. the reclock signal, is the decoded data signal, as shown by the waveform 158 of FIG. 4, illustration (p). Comparing FIG. 4 illustration (a) with illustration (p) it is seen that the decoded signal replicates the rotating frame data signal, with a one bit interval shift, i.e. one transparent asynchronous xceiver (transceiver) interface clock period.

Similarly, the decoding circuitry decodes the absence of pulses as logic one bit states. With the appearance of the second pulse group in waveform 110, a "00", the SELECT signal enables the decode circuitry 122 for the first bit interval of pulses and enables circuitry 124 for the second group of four pulses. Each of these encoded bits is decoded in the same manner as described hereinabove.

In the present embodiment the encoding algorithm is simplified by the use of a limited number of pulses and a simple rules based decoding algorithm which requires a simple majority for translating the received pulses into a logic zero. In the embodiment shown, three pulses occurring within a bit interval is translated as a logic zero and less than three as a logic one. This is based on empirical observations of the signal noise characteristics of a CT rotating interface. A four pulse encoding pattern is found to be sufficient in ensuring the integrity of the coupled data in its transfer across the CT rotating interface. However, it should be understood that greater or lesser numbers of pulses may be used, as well as greater complexity pulse patterns and decoding algorithms, as may be deemed necessary by those skilled in the art for a particular application. Also, the disclosed embodiments of the signal transmitter and signal receiver may be altered or completely reconfigured as necessary to achieve the various encoding patterns and decoding algorithms that may be used.

The present invention provides high noise immunity to high speed data signals coupled across a rotating interface. The digital encoding of one of the two states of the data signal with an RF pulse pattern provides a simpler, lower cost, more effective method of ensuring data integrity than the prior art methods or apparatus. Similarly, although the invention has been shown and described with respect to a best mode embodiment thereof, it should be understood by those skilled in the art that various changes, omissions, and additions may be made to the form and detail of the disclosed embodiment without departing from the spirit and scope of the invention, as recited in the following claims.

What is claimed is:

1. A computerized tomography system, comprising:
   a rotating frame, having an aperture adapted to rotationally encircle a test object placed in an image plane therein, and including an x-ray source and a detector array each disposed on opposite sides of said aperture, said source emitting x-rays within said image plane at each of several angular positions along the rotational path of the aperture and said detector array receiving said emitted x-rays which pass through the test object, said detector array providing a plurality of detectors and adapted for rotation in an image plane coincident with selected axial positions within said aperture, said first frame thereof, said detector array providing an image signal indication of the intensity of the x-rays received thereby, said image signal indication comprising a serial digital bit data signal, each said serial digital bit occurring in an associated bit interval and at a data signal bit speed, and each representing, alternatively, a first logic state and a second logic state which, collectively, are representative of a view of the test object at the related angular position of the aperture;
   a stationary frame, in fixed relation to said rotating frame, and including a signal processor with memory for receiving said serial digital bit data signal associated with each said view at each said angular position, for providing a cross-sectional image of the test object as a composite of said views;

a signal transmitter disposed on said rotating frame for encoding said serial digital bit data signal with a digital radio frequency (RF) carrier signal to provide a digitally encoded serial digital bit data signal; wherein said signal transmitter digitally encodes only the bit intervals associated with each first logic state bit of said serial digital bit data signal; electromagnetic coupler having first and second elements disposed on said rotating frame and said stationary frame, respectively, said first element receiving said encoded serial digital bit data signal from said signal transmitter for providing electromagnetic coupling thereof to said second element; and a signal receiver disposed on said second frame and responsive to said second element, for translating said digitally encoded serial digital bit data signal to its pre-encoded state; wherein said signal receiver translates the received first logic state encoded signal into first logic state bits and second logic state bits in correspondence with the pre-encoded state of said serial digital bit data signal.

2. The system of claim 1, wherein said signal transmitter encodes each said bit interval of each said first logic state bit with a plurality of serial pulses occurring at an RF pulse repetition frequency.

3. The system of claim 2, wherein:

said signal transmitted further including a transmitter clock and a phase locked loop for providing a transparent asynchronous xceiver (transceiver) interface clock signal which is synchronized to said data signal bit speed, and which controls the occurrence of the bit intervals of said digitally encoded serial digital bit data signal to provide synchronization thereof with said data signal bit speed; and said signal receiver includes signal detection circuitry for recovering said transparent asynchronous xceiver (transceiver) interface signal from the received said digitally encoded serial digital bit data signal, to provide said translation in synchronization with said data signal bit speed.

4. The system of claim 3, wherein:

said signal transmitter encodes each said bit interval of each said first logic state bit with a known even number of serial pulses occurring at an RF pulse repetition frequency; and said signal receiver translates each presence of a majority of said known even number of serial pulses within a bit interval as a first logic state signal bit and translates each other number occurrence of serial pulses as a second logic state signal bit.

5. The system of claim 3, wherein:

said signal transmitter encodes each said bit interval of each said first logic state bit with a known even number of serial pulses occurring at an RF pulse repetition frequency; and said signal receiver detects the presence of each bit interval from said transparent asynchronous xceiver (transceiver) interface clock signal, and counts the occurrence of serial pulses within each detected bit interval, said receiver translating each presence of a majority of said known even number of serial pulses within said detected bit interval as a first logical state signal bit, said receiver translating each other number occurrence of serial pulses as a second logic state signal bit.

6. The system of claim 3, wherein:

said signal transmitter encodes each said bit interval of each said first logic state bit with four serial pulses occurring at an RF pulse repetition frequency; and said signal receiver detects the presence of each bit interval from said transparent asynchronous xceiver (transceiver) interface clock signal, and counts the occurrence of serial pulses within each detected bit interval, said receiver translating each presence of three of four and four of four pulses within each detected bit interval as a first logic state signal bit, said receiver translating each presence of no pulses and one of four pulses and three of four pulses within each said detected bit interval as a second logic state signal bit.

7. The system of claim 3, wherein said electromagnetic coupler comprises an RF slipring.

8. The system of claim 7, wherein said signal transmitter provides said four serial pulses at an RF pulse repetition frequency which is at least four times greater than the frequency corresponding to the data signal bit speed.

9. The system of claim 7, wherein said signal transmitter provides said four serial pulses at a substantially fifty percent duty cycle.

10. The system of claim 1, wherein:

said signal transmitter further includes a phase locked loop for providing a transparent asynchronous xceiver (transceiver) interface clock signal which is synchronized to said data signal bit speed, and which controls the occurrence of the bit intervals of said digitally encoded serial digital bit data signal to provide synchronization thereof with said data signal bit speed; and said signal receiver includes signal detection circuitry for recovering said transparent asynchronous xceiver (transceiver) interface clock signal from the received said digitally encoded serial digital bit data signal, to provide said translation in synchronization with said data signal bit speed.

11. The system of claim 1, wherein said signal transmitter and said signal receiver each comprise emitter coupled logic (ECL) circuit elements.

12. The system of claim 11, wherein said ECL circuit elements are positive ECL (PECL).

13. Apparatus for coupling a serial digital bit signal from a first surface to a second surface which is in relative rotation therewith, the serial digital bit signal comprising signal bits each occurring in an associated bit interval and at a signal bit speed, and each signal bit representing, alternatively, a first logic state and a second logic state, the apparatus comprising:

a signal transmitter disposed on said first surface for encoding said serial digital bit signal with a digital radio frequency (RF) carrier signal to provide a digitally encoded serial digital bit data signal, wherein said signal transmitter digitally encodes only the bit intervals associated with each first logic state bit of said serial digital bit data signal;

electromagnetic coupler having first and second elements disposed on said rotating frame and said stationary frame, respectively, said first element receiving said encoded serial digital bit signal from said signal transmitter for providing electromagnetic coupling thereof to said second element; and a signal receiver disposed on said second frame and responsive to said second element, for translating said digitally encoded serial digital bit signal to its pre-encoded state, wherein said signal receiver translates the received first logic state encoded signal into first logic state bits and second logic state bits in correspondence with the pre-encoded state of said serial digital bit data signal.

14. The apparatus of claim 13, wherein said signal transmitter encodes each said bit interval of each said first logic state bit with a plurality of serial pulses occurring at an RF pulse repetition frequency.

15. The apparatus of claim 14, wherein
said signal transmitter further including a transmitter clock and a phase locked loop for providing a transparent asynchronous xceiver (transceiver) interface clock signal which is synchronized to said data signal bit speed, and which controls the occurrence of the bit intervals of said digitally encoded serial digital bit data signal to provide synchronization thereof with said data signal bit speed; and
said signal receiver includes signal detection circuitry for recovering said transparent asynchronous xceiver (transceiver) interface clock signal from the received said digitally encoded serial digital bit data signal, to provide said translation in synchronization with said data signal bit speed.

16. The apparatus of claim 15, wherein:
said signal transmitter encodes each said bit interval of each said first logic state bit with a known even number of serial pulses occurring at an RF pulse repetition frequency; and
said signal receiver translates each presence of a majority of said known even number of serial pulses within a bit interval as a first logic state signal bit and translates each other number occurrence of serial pulses as a second logic state signal bit.

17. The apparatus of claim 15, wherein:
said signal transmitter encodes each said bit interval of each said first logic state bit with a known even number of serial pulses occurring at an RF pulse repetition frequency; and
said signal receiver detects the presence of each bit interval from said transparent asynchronous xceiver (transceiver) interface clock signal, and counts the occurrence of serial pulses within each detected bit interval, said receiver translating each presence of a majority of said known even number of serial pulses within said detected bit interval as a first logic state signal bit, said receiver translating each other number occurrence of serial pulses as a second logic state signal bit.

18. The apparatus of claim 15, wherein:
said signal transmitter encodes each said bit interval of each said first logic state bit with four serial pulses occurring at an RF pulse repetition frequency; and
said signal receiver detects the presence of each bit interval from said transparent asynchronous xceiver (transceiver) interface clock signal, and counts the occurrence of serial pulses within each detected bit interval, said receiver translating each presence of three of four and four of four pulses within said detected bit interval as a first logic state signal bit, said receiver translating each presence of no pulses and one of four pulses and three of four pulses within each said detected bit interval as a second logic state signal bit.

19. The apparatus of claim 18, wherein:
said signal transmitter provides said four serial pulses at an RF pulse repetition frequency which is at least four times greater than the frequency corresponding to the data signal bit speed.

20. The apparatus of claim 18, wherein said signal transmitter provides said four serial pulses at a substantially fifty percent duty cycle.

21. The apparatus of claim 13, wherein:
said signal transmitter further including a transmitter clock and a phase locked loop for providing a transparent asynchronous xceiver (transceiver) interface clock signal which is synchronized to said data signal bit speed, and which controls the occurrence of the bit intervals of said digitally encoded serial digital bit data signal to provide synchronization thereof with said data signal bit speed; and
said signal receiver includes signal detection circuitry for recovering said transparent asynchronous xceiver (transceiver) interface clock signal from the received said digitally encoded serial digital bit data signal, to provide said translation in synchronization with said data signal bit speed.

22. The apparatus of claim 13, wherein said signal transmitter and said signal receiver each comprise emitter coupled logic (ECL) circuit elements.

23. A method of transferring signal data across the rotating interface of a computerized tomography system of the type having a rotating frame mounted in a relatively stationary frame, the rotating frame having an aperture adapted to rotationally encircle a test object placed in an image plane therein for obtaining x-ray views of the test object at one or more angular positions of the rotating frame, each view comprising a serial digital bit data signal, each said serial digital bit occurring in an associated bit interval and at a data signal bit speed, and each representing, alternatively, a first logic state and a second logic state which represent, collectively, the desired view, such serial digital bit data signal associated with each view being provided to a signal processor mounted to the relatively stationary frame, the signal processor providing a cross section image of the test object as a composite of all such views, the method comprising the steps of:
encoding the serial digital bit data signal on the rotating frame by identifying the presence of each bit interval, detecting from among the identified bit intervals those occurring with a first logic state bit, and modulating each such first logic state bit interval with a digital radio frequency (RF) carrier signal to provide a digitally encoded serial digital bit data signal;
using an electromagnetic coupler having first and second elements disposed on the rotating frame and the stationary frame, respectively, and presenting the digitally encoded serial digital bit signal to the first element which provides electromagnetic coupling thereof to the second element; and
receiving the digitally encoded serial digital bit data signal from the second element and translating the encoded signal to its pre-encoded state.

24. The method of claim 23, wherein said step of modulating comprises the step of:
replacing the first logic state signal bit with a plurality of serial pulses occurring at an RF pulse repetition frequency.

25. The method of claim 24, further comprising the steps of:
providing a transparent asynchronous xceiver (transceiver) interface clock signal on the rotating frame;
synchronizing said transparent asynchronous xceiver (transceiver) interface clock signal with the data signal bit speed;

using the synchronized transparent asynchronous xceiver (transceiver) interface clock signal to control the occurrence of the bit intervals of the digitally encoded serial digital bit data signal on the rotating frame, so as to provide synchronization thereof with the data signal bit speed; and extracting the transparent asynchronous xceiver (transceiver) interface clock signal at the stationary frame from the received digitally encoded serial digital bit data signal, to provide said translation in synchronization with said data signal bit speed.

26. The method of claim 25, wherein:

said step of replacing comprises the step of:

providing said plurality of serial pulses a known even number of serial pulses occurring at an RF pulse repetition frequency; and said step of translating comprises the steps of:

recording each presence of a majority of said known even number of serial pulses within a bit interval as a first logic state signal bit and recording each other number occurrence of serial pulses as a second logic state signal bit.

27. The method of claim 25, wherein:

said step of replacing comprises the step of:

providing said plurality of serial pulses a known even number of serial pulses occurring at an RF pulse repetition frequency; and said step of translating comprises the steps of:

detecting the presence of each bit interval as determined from said transparent asynchronous xceiver (transceiver) interface clock signal;

counting the occurrence of serial pulses within each such detected bit interval; and recording each presence of a majority of said known even number of serial pulses within said detected bit interval as a first logic state signal bit, and recording each other number occurrences of serial pulses as a second logic state signal bit.

28. The method of claim 25, wherein:

said step of replacing comprises the step of:

providing four serial pulses occurring at an RF pulse repetition frequency; and said step of translating comprises the steps of:

detecting the presence of each bit interval as determined from said taxi clock signal; recording the occurrence of three of four and four of four pulses within said detected bit interval as a first logic state signal bit, and recording each presence of no pulses and one of four pulses and three of four pulses within said detected bit interval as a second logic state signal bit.

* * * * *

UNITED STATES PATENT AND TRADEMARK OFFICE
CERTIFICATE OF CORRECTION

PATENT NO. : 6,181,766 B1
DATED : January 30, 2001
INVENTOR(S) : Phil E. Pearson, Jr., et al.

It is certified that error appears in the above-identified patent and that said Letters Patent is hereby corrected as shown below:

<u>Column 6,</u>
Line 3, delete "taxi".

Signed and Sealed this

Sixteenth Day of October, 2001

*Attest:*

NICHOLAS P. GODICI
*Attesting Officer*  *Acting Director of the United States Patent and Trademark Office*